United States Patent
Mimura

(10) Patent No.: US 10,748,283 B2
(45) Date of Patent: Aug. 18, 2020

(54) IMAGE PROCESSING DEVICE AND PROGRAM

(71) Applicant: Konica Minolta, Inc., Chiyoda-ku, Tokyo (JP)

(72) Inventor: Yusuke Mimura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 124 days.

(21) Appl. No.: 16/064,667

(22) PCT Filed: Dec. 22, 2016

(86) PCT No.: PCT/JP2016/088292
§ 371 (c)(1),
(2) Date: Jun. 21, 2018

(87) PCT Pub. No.: WO2017/110974
PCT Pub. Date: Jun. 29, 2017

(65) Prior Publication Data
US 2019/0012786 A1    Jan. 10, 2019

(30) Foreign Application Priority Data
Dec. 24, 2015 (JP) .................... 2015-251169

(51) Int. Cl.
*G01N 33/53* (2006.01)
*G06T 7/00* (2017.01)
(Continued)

(52) U.S. Cl.
CPC .......... *G06T 7/0012* (2013.01); *G01N 33/53* (2013.01); *G06K 9/0014* (2013.01);
(Continued)

(58) Field of Classification Search
CPC combination set(s) only.
See application file for complete search history.

(56) References Cited

U.S. PATENT DOCUMENTS

2007/0105136 A1* 5/2007 Staudt .................... G16B 25/00
                                                           435/6.16
2009/0005693 A1* 1/2009 Brauner ................. A61B 6/508
                                                           600/481
(Continued)

FOREIGN PATENT DOCUMENTS

JP    2012208106 A    10/2012
JP    2013150616 A     8/2013
(Continued)

OTHER PUBLICATIONS

International Search Report corresponding to Application No. PCT/JP2016/088292; dated Apr. 4, 2017.
(Continued)

*Primary Examiner* — Omar S Ismail
(74) *Attorney, Agent, or Firm* — Cantor Colburn LLP

(57) ABSTRACT

An image processing device and a program capable of extracting a cell region as a diagnosis target more accurately may be provided. An image processing device is characterized by: first extraction means (control unit 21) for extracting a candidate region from a form image representing a form of a cell in a tissue sample; acquisition means (control unit 21) for acquiring biological substance information on at least one kind of the biological substance from images representing expression of one or more kinds of biological substances in the tissue sample; and second extraction means (control unit 21) for extracting a diagnosis target region from the candidate region based on characteristic information indicating characteristics of the candidate region and/or the biological substance information.

10 Claims, 10 Drawing Sheets

(51) Int. Cl.
*G16B 40/00* (2019.01)
*G06T 7/11* (2017.01)
*G06K 9/46* (2006.01)
*G06K 9/00* (2006.01)
*G06K 9/38* (2006.01)
*G06K 9/32* (2006.01)

(52) U.S. Cl.
CPC ............ *G06K 9/3241* (2013.01); *G06K 9/38* (2013.01); *G06K 9/4652* (2013.01); *G06T 7/11* (2017.01); *G16B 40/00* (2019.02); *G06T 2207/10056* (2013.01); *G06T 2207/30024* (2013.01)

(56) References Cited

U.S. PATENT DOCUMENTS

| | | | | |
|---|---|---|---|---|
| 2010/0111396 | A1* | 5/2010 | Boucheron | G06K 9/0014 382/133 |
| 2011/0074944 | A1* | 3/2011 | Can | G01N 21/6428 348/79 |
| 2011/0103657 | A1* | 5/2011 | Kang | G06K 9/4609 382/128 |
| 2014/0043461 | A1* | 2/2014 | Otsuka | G06T 7/0012 348/79 |
| 2014/0118524 | A1* | 5/2014 | Munck | G01N 21/6408 348/79 |
| 2014/0119621 | A1* | 5/2014 | Uber, III | G01R 33/5601 382/128 |
| 2014/0227682 | A1* | 8/2014 | Seth | G06K 9/00147 435/5 |
| 2014/0350395 | A1* | 11/2014 | Shachaf | A61B 5/444 600/431 |
| 2015/0132766 | A1* | 5/2015 | Yasuda | G01N 21/6458 435/7.1 |
| 2016/0035100 | A1* | 2/2016 | Bamford | G01J 3/4406 382/131 |
| 2016/0314580 | A1* | 10/2016 | Lloyd | G06K 9/0014 |
| 2016/0321495 | A1* | 11/2016 | Chukka | G06T 7/0014 |
| 2017/0186156 | A1* | 6/2017 | Isoda | G06T 7/90 |

FOREIGN PATENT DOCUMENTS

| | | |
|---|---|---|
| JP | 2013238459 A | 11/2013 |
| WO | 2013148448 A1 | 10/2013 |

OTHER PUBLICATIONS

Written Opinion of the International Searching Authority corresponding to Application No. PCT/JP2016/088292; dated Apr. 4, 2017.

JPO Notice of Reasons for Refusal corresponding to Application No. 2017-558245; dated Sep. 17, 2019.

European Office Action corresponding to Application No. 16878861.0-1111; dated Aug. 7, 2019.

Extended European Search Report corresponding to Application No. 16878861.0-1111 PCT/JP2016088292; dated Sep. 10, 2018.

* cited by examiner

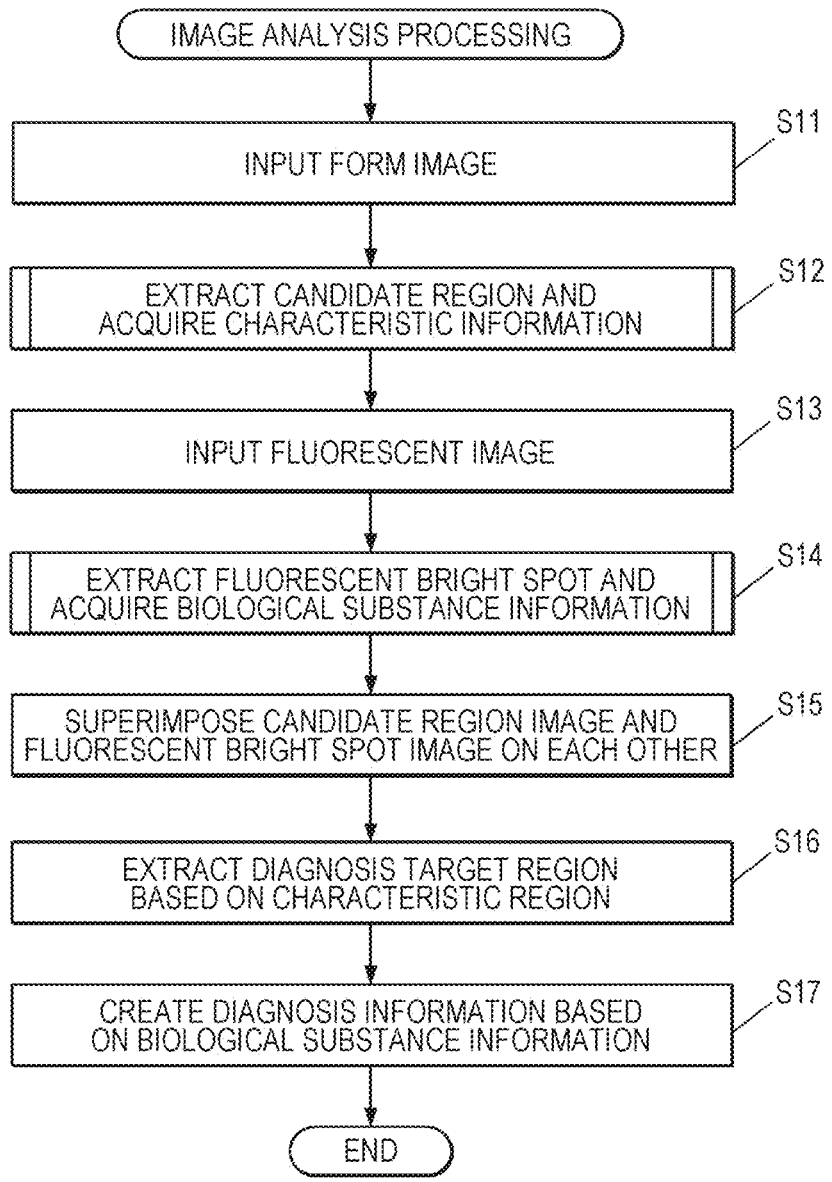

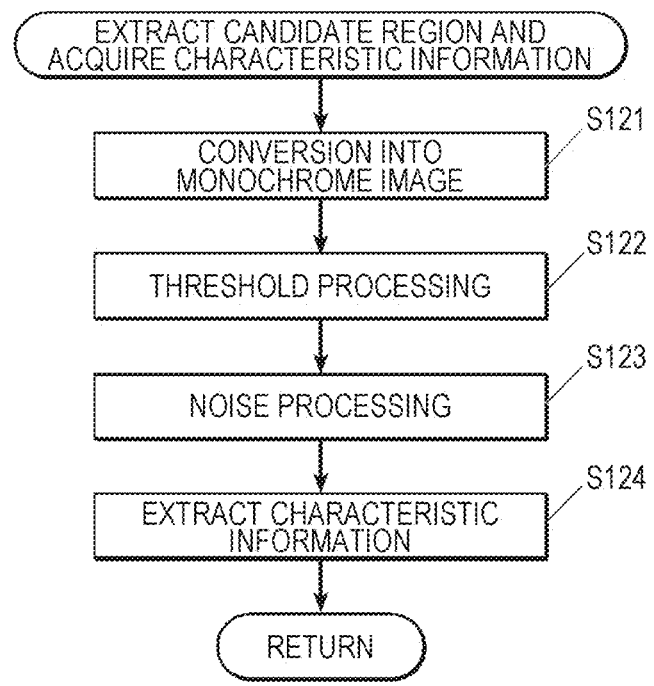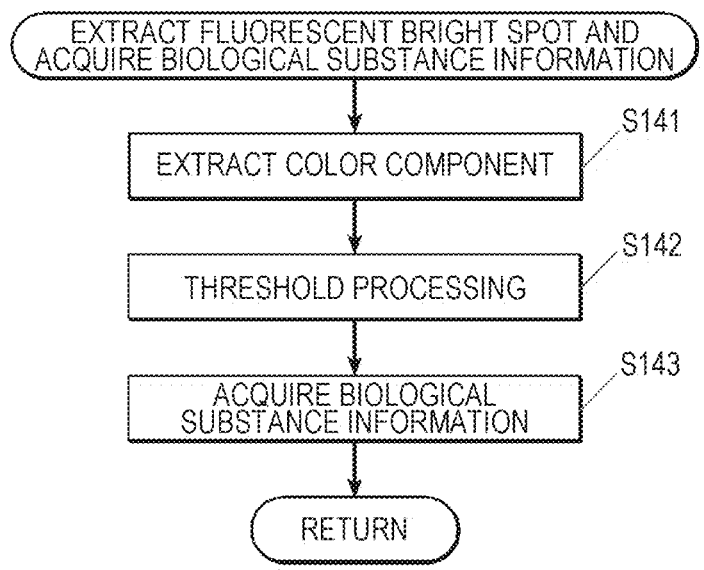

IMAGE PROCESSING DEVICE AND PROGRAM

CROSS REFERENCE TO RELATED APPLICATIONS

This is a U.S. national stage of application No. PCT/JP2016/088292, filed on Dec. 22, 2016. Priority under 35 U.S.C. § 119(a) and 35 U.S.C. § 365(b) is claimed from Japanese Patent Application No. 2015-251169, filed on Dec. 24, 2015, the disclosure of which is also incorporated herein by reference.

TECHNICAL FIELD

The present invention relates to an image processing device and a program.

BACKGROUND ART

In recent years, with spread of molecular target drug therapy focusing on an antibody drug, quantification of a biological substance on an observation target cell is required in order to design a molecular target drug more effectively. As a method for confirming presence of a biological substance, a tissue analysis method based on combination of a fluorescent substance bonded to a biological substance recognition site and a biological substance corresponding to the biological substance recognition site is known.

For example, Patent Literature 1 describes a method for staining a specific antigen of a tissue section with a plurality of fluorescent substance-containing nanoparticles and generating information on the specific antigen in the section based on a fluorescent signal of the nanoparticles.

According to the method described in Patent Literature 1, a fluorescent signal is observed in a form of dots without being buried in autofluorescence or the like of a tissue by using fluorescent substance-containing nanoparticles of high brightness as a fluorescent labeling material. This makes it easy to measure the number of a biological substance per cell based on a fluorescent signal of nanoparticles.

CITATION LIST

Patent Literature

Patent Literature 1: JP 2012-208106 A

SUMMARY OF INVENTION

Technical Problem

However, in fact, for example, in an image obtained by photographing a tissue sample used for cancer diagnosis, in addition to a cancer cell as a diagnosis target, a fibroblast which is an interstitial tissue, a vascular endothelial cell, a myoepithelium cell, a lymphocyte, and the like are observed.

According to the method described in Patent Literature 1, such an interstitial tissue is also extracted as a cell region together with a cell as a diagnosis target. In a case where expression of a biological substance characteristic of cancer is observed in the extracted cell region, it is found that the cell region is a cancer cell as a diagnosis target. However, in a case where expression of a biological substance characteristic of cancer is not observed, it cannot be determined whether the cell region is a cancer cell in which a biological substance characteristic of cancer is not expressed or a cell which is not a diagnosis target (interstitial tissue).

Therefore, according to the method described in Patent Literature 1, it is not possible to extract only a region of a cancer cell as a diagnosis target. Therefore, an error occurs in diagnosis support information such as the number of a biological substance per cell as a diagnosis target, and this may lead to misdiagnosis.

A main object of the present invention is to provide an image processing device and a program capable of extracting a cell region as a diagnosis target more accurately.

The above problems according to the present invention can be solved by the following means.

Solution to Problem

1. An image processing device including:
   first extraction means for extracting a candidate region from a form image representing a form of a cell in a tissue sample;
   acquisition means for acquiring biological substance information on at least one kind of the biological substance from images representing expression of one or more kinds of biological substances in the tissue sample; and
   second extraction means for extracting a diagnosis target region from the candidate region based on characteristic information indicating characteristics of the candidate region and/or the biological substance information.

2. The image processing device according to the first item, in which
   the second extraction means extracts the diagnosis target region based on at least the characteristic information, and
   the characteristic information includes at least one of a shape, an area, and a position of the candidate region.

3. The image processing device according to the first or second item, in which
   the second extraction means extracts the diagnosis target region based on at least the biological substance information, and
   the biological substance information includes at least one of a position, the number, and density of the biological substance.

4. The image processing device according to any one of the first to third items, in which
   the acquisition means acquires biological substance information on the plurality of kinds of biological substances from the images representing expression of the plurality of kinds of biological substances in the tissue sample, and
   the second extraction unit extracts the diagnosis target region based on at least the biological substance information on a first biological substance.

5. The image processing device according to any one of the first to fourth items, further including creation means for creating diagnosis support information in the diagnosis target region extracted by the second extraction means based on the biological substance information.

6. The image processing device according to the fourth item, further including creation means for creating diagnosis support information in the diagnosis target region extracted by the second extraction means based on the biological substance information on a second biological substance.

7. A program for causing a computer to function as:
   first extraction means for extracting a candidate region from a form image representing a form of a cell in a tissue sample;
   acquisition means for acquiring biological substance information on at least one kind of the biological substance from images representing expression of one or more kinds of biological substances in the tissue sample; and second extraction means for extracting a diagnosis target region from the candidate region based on characteristic information indicating characteristics of the candidate region and/or the biological substance information.

Advantageous Effects of Invention

According to the present invention, a cell region as a diagnosis target can be extracted more accurately.

BRIEF DESCRIPTION OF DRAWINGS

FIG. 3 is a flowchart illustrating image analysis processing in a first embodiment.

FIG. 4 is a flowchart illustrating a flow of a step for extracting a candidate region.

FIG. 5 is a flowchart illustrating a flow of a step for extracting a fluorescent bright spot.

DESCRIPTION OF EMBODIMENTS

Hereinafter, embodiments for performing the present invention will be described with reference to the drawings, but the present invention is not limited thereto.

<Configuration of Pathological Diagnosis Support System 100>

Figure 1:
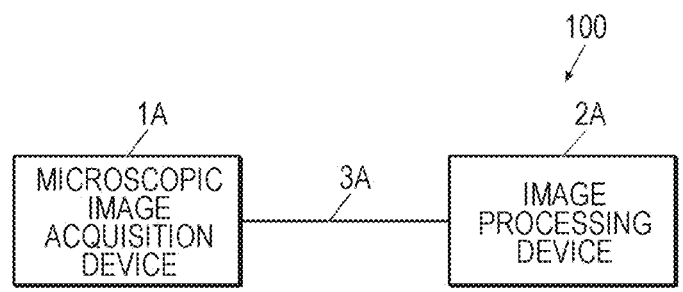
FIG. 1 is a diagram illustrating a system configuration of a diagnosis support information generation system.

FIG. 1 illustrates an overall configuration example of a pathological diagnosis support system 100.

The pathological diagnosis support system 100 acquires a microscopic image of a tissue section of a human body stained with a predetermined staining reagent and analyzes the acquired microscopic image to output a characteristic quantity quantitatively representing expression of a specific biological substance in the tissue section as an observation target.

As illustrated in FIG. 1, in the pathological diagnosis support system 100, a microscopic image acquisition device 1A and an image processing device 2A are connected to each other so as to be able to transmit and receive data via an interface such as a cable 3A.

A connection method between the microscopic image acquisition device 1A and the image processing device 2A is not particularly limited. For example, the microscopic image acquisition device 1A and the image processing device 2A may be connected to each other by a local area network (LAN) or wirelessly.

The microscopic image acquisition device 1A is a well-known microscope with a camera, acquires a microscopic image of a tissue section on a slide placed on a slide fixing stage, and transmits the microscopic image to the image processing device 2A.

The microscopic image acquisition device 1A includes irradiation means, image-forming means, imaging means, a communication I/F, and the like. The irradiating means includes a light source, a filter, and the like, and irradiates a tissue section on a slide placed on a slide fixing stage with light. The image-forming means includes an eyepiece lens, an objective lens, and the like, and forms an image of transmitted light, reflected light, or fluorescence emitted from a tissue section on a slide due to irradiation light. The imaging means is a microscope installation camera including a charge coupled device (CCD) sensor and the like and imaging an image formed on an image plane by the image-forming means to generate digital image data of a microscopic image. The communication I/F transmits generated image data of a microscopic image to the image processing device 2A.

The microscopic image acquisition device 1A includes a bright field unit combining irradiation means and image-forming means suitable for bright field observation and a fluorescence unit combining irradiation means and image-forming means suitable for fluorescence observation. By switching the units, the bright field and fluorescence can be switched with each other.

Note that any known microscope (for example, a phase contrast microscope, a differential interference microscope, or an electron microscope) with a camera installed therein can be used as the microscopic image acquisition device 1A.

Note that the microscopic image acquisition device 1A is not limited to a microscope with a camera. For example, a virtual microscope slide creation device (for example, refer to JP 2002-514319 A) that scans a slide on a slide fixing stage of a microscope to acquire a microscopic image of the entire tissue section may be used. The virtual microscope slide creation device can acquire image data capable of viewing an image of the entire tissue section on a slide at a time on a display unit.

The image processing device 2A analyzes a microscopic image transmitted from the microscopic image acquisition device 1A to calculate an expression distribution of a specific biological substance in a tissue section as an observation target.

Figure 2:
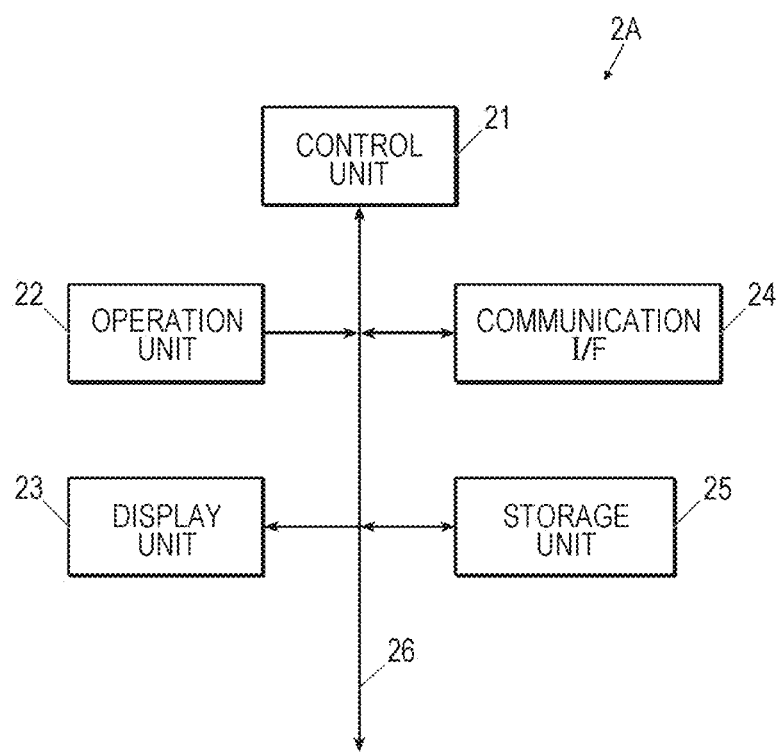
FIG. 2 is a block diagram illustrating a functional configuration of the image processing device of FIG. 1.

FIG. 2 illustrates an example of a functional configuration of the image processing device 2A.

As illustrated in FIG. 2, the image processing device 2A includes a control unit 21, an operation unit 22, a display unit 23, a communication I/F 24, a storage unit 25, and the like, and these units are connected to each other via a bus 26.

The control unit 21 includes a central processing unit (CPU), a random access memory (RAM), and the like, executes various processes in cooperation with various programs stored in the storage unit 25, and controls operation of the image processing device 2A integrally.

For example, the control unit 21 executes image analysis processing in cooperation with an image processing program stored in the storage unit 25 to realize functions as first extraction means, acquisition means, second extraction means, and creation means.

The operation unit 22 includes a keyboard including a character input key, a numeric input key, various function keys, and the like, and a pointing device such as a mouse, and outputs a depression signal of a key pressed in a keyboard and an operation signal of a mouse to the control unit 21 as input signals.

The display unit 23 includes a monitor such as a cathode ray tube (CRT) or a liquid crystal display (LCD) and displays various screens according to an instruction of a display signal input from the control unit 21.

The communication I/F 24 is an interface for transmitting and receiving data with an external device such as the microscopic image acquisition device 1A.

The storage unit 25 includes, for example, a hard disk drive (HDD) and a semiconductor nonvolatile memory. The storage unit 25 stores various programs and various data as described above.

Besides, the image processing device 2A may include a LAN adapter, a router, and the like and may be connected to an external device via a communication network such as a LAN.

<Regarding Image>

In the present embodiment, for example, the image processing device 2A preferably performs analysis using an image representing expression of a specific biological substance in a cell (for example, a fluorescent image representing expression of a specific biological substance in a cell as a fluorescent bright spot) transmitted from the microscopic image acquisition device 1A and a form image (for example, a bright field image) representing a form of a predetermined structure of a cell, such as a cell nucleus or a cell membrane.

The "bright field image" is, for example, a microscopic image obtained by forming an enlarged image of a tissue section stained with a hematoxylin staining reagent (H staining reagent) and a hematoxylin-eosin staining reagent (HE staining reagent) and photographing the tissue section in a bright field in the microscopic image acquisition device 1A and is a cell form image representing a form of a cell in the tissue section. Hematoxylin (H) is a blue-purple dye and stains a cell nucleus, a bone tissue, a part of a cartilage tissue, a serous component (basophilic tissue or the like), and the like. Eosin (E) is a red to pink dye and stains a cytoplasm, a soft tissue connective tissue, an erythrocyte, a fibrin, an endocrine granule (eosinophilic tissue or the like), and the like.

As the cell form image, in addition to the bright field image, a fluorescent image obtained by staining a tissue section with a fluorescent staining reagent capable of specifically staining a structure of a cell as a diagnosis target, and photographing fluorescence emitted by the fluorescent staining reagent used may be used. Examples of the fluorescent staining reagent that can be used for acquiring a form image include a DAPI staining reagent capable of staining a cell nucleus and Papalonicolaou staining reagent capable of staining a cytoplasm. In addition, a phase contrast image, a differential interference image, an electron microscopic image, or the like may be used as a form image.

A fluorescent image representing expression of a specific biological substance in a cell as a fluorescent bright spot is a microscopic image obtained by irradiating a tissue section stained with a fluorescent staining reagent containing a fluorescent substance or a fluorescent substance-containing nanoparticle that is specifically bonded to and/or reacts with a specific biological substance with excitation light of a predetermined wavelength in the microscopic image acquisition device 1A to cause the fluorescent substance to emit fluorescence and forming an enlarged image of the fluorescence and photographing the fluorescence. Note that the "fluorescent substance-containing nanoparticle" is a nanoparticle containing a fluorescent substance and will be described in detail below.

<Fluorescent Staining Reagent, Staining Method, and the Like>

Hereinafter, a fluorescent staining reagent for acquiring a fluorescent image representing expression of a specific biological substance specifically expressed in a cell as a fluorescent bright spot and a method for staining a tissue section using the fluorescent staining reagent will be described.

(1) Fluorescent Substance

Examples of a fluorescent substance used for a fluorescent staining reagent include a fluorescent organic dye and a quantum dot (semiconductor particle). When being excited by ultraviolet to near-infrared light having a wavelength within a range of 200 to 700 nm, the fluorescent substance preferably emits visible to near-infrared light having a wavelength within a range of 400 to 1100 nm.

Examples of the fluorescent organic dye include a fluorescein-based dye molecule, a rhodamine-based dye molecule, an Alexa Fluor (manufactured by Invitrogen Corporation)-based dye molecule, a BODIPY (manufactured by Invitrogen Corporation)-based dye molecule, a cascade-based dye molecule, a coumarin-based dye molecule, an eosin-based dye molecule, an NBD-based dye molecule, a pyrene-based dye molecule, a Texas Red-based dye molecule, and a cyanine-based dye molecule.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (manufactured by Invitrogen Corporation), methoxycoumarin, eosin, NBD, pyrene, Cy5, Cy5.5, and Cy7. These fluorescent organic dyes may be used singly or in combination of a plurality of kinds thereof.

As the quantum dot, any one of a quantum dot containing a II-VI group compound, a quantum dot containing a III-V group compound, and a quantum dot containing a IV group compound (also referred to as a "II-VI group quantum dot", a "III-V group quantum dot", and a "IV group quantum dot", respectively) can be used. These quantum dots may also be used singly or in combination of a plurality of kinds thereof.

Specific examples thereof include CdSe, CdS, CdTe, ZnSe, ZnS, ZnTe, InP, InN, InAs, InGaP, GaP, GaAs, Si, and Ge, but are not limited thereto.

A quantum dot having the above-described quantum dot as a core and having a shell disposed on the core can also be used. In the description below, as a notation of a quantum dot having a shell, a case where the core is CdSe and the shell is ZnS is denoted by CdSe/ZnS.

Examples of the quantum dot include CdSe/ZnS, CdS/ZnS, InP/ZnS, InGaP/ZnS, Si/SiO$_2$, Si/ZnS, Ge/GeO$_2$, and Ge/ZnS, but are not limited thereto.

The quantum dot may be surface-treated with an organic polymer or the like, if necessary. Examples thereof include CdSe/ZnS (manufactured by Invitrogen Corporation) having a surface carboxy group and CdSe/ZnS (manufactured by Invitrogen Corporation) having a surface amino group.

(2) Fluorescent Substance-Containing Nanoparticle

The "fluorescent substance-containing nanoparticle" is a nanoparticle containing a fluorescent substance as described above and specifically means a nanoparticle having a fluorescent substance dispersed therein. The fluorescent substance and the nanoparticle itself may be chemically bonded to each other or need not to be bonded to each other.

A material constituting the nanoparticle is not particularly limited, and examples thereof include silica, polystyrene, polylactic acid, and melamine.

The fluorescent substance-containing nanoparticle can be manufactured by a known method.

For example, a silica nanoparticle containing a fluorescent organic dye can be synthesized with reference to synthesis of a FITC-containing silica particle described in Langmuir Vol. 8, p. 2921 (1992). By using a desired fluorescent organic dye in place of FITC, various fluorescent organic dye-containing silica nanoparticles can be synthesized.

A silica nanoparticle containing a quantum dot can be synthesized with reference to synthesis of a CdTe-containing silica nanoparticle described in New Journal of Chemistry Vol. 33, p. 561 (2009).

A polystyrene nanoparticle containing a fluorescent organic dye can be manufactured by a copolymerization method using an organic dye having a polymerizable functional group described in U.S. Pat. No. 4,326,008 (1982) or a fluorescent organic dye impregnation method into a polystyrene nanoparticle described in U.S. Pat. No. 5,326,692 (1992).

A polymer nanoparticle containing a quantum dot can be manufactured by a quantum dot impregnation method into a polystyrene nanoparticle described in Nature and Biotechnology Vol. 19, p. 631 (2001).

The average particle diameter of the fluorescent substance-containing nanoparticles is not particularly limited, but particles having a particle diameter of about 30 to 800 nm can be used. In addition, a coefficient of variation (=(standard deviation/average value)×100%) indicating variation in particle diameter is not particularly limited, but particles having a coefficient of variation of 20% or less are preferably used.

The average particle diameter is a value obtained by photographing an electron microscopic photograph using a scanning electron microscope (SEM), measuring the cross-sectional areas of a sufficient number of particles, and determining a diameter of a circle as a particle diameter when each of the measured values is assumed to be the area of a circle. In the present embodiment, an arithmetic average of the particle diameters of 1000 particles is taken as the average particle diameter. The coefficient of variation is also a value calculated from a particle diameter distribution of 1000 particles.

(3) Bonding Between Biological Substance Recognition Site and Fluorescent Substance-Containing Nanoparticle In the present embodiment, a case where a reagent in which a fluorescent substance-containing nanoparticle and a biological substance recognition site are directly bonded to each other in advance is used as a fluorescent staining reagent that is specifically bonded to and/or reacts with a specific biological substance will be described as an example. The "biological substance recognition site" is a site that is specifically bonded to and/or reacts with a specific biological substance.

The specific biological substance is not particularly limited as long as there is a substance that is specifically bonded thereto, but representative examples thereof include a protein (peptide) and a nucleic acid (oligonucleotide and polynucleotide).

Therefore, examples of the biological substance recognition site include an antibody that recognizes the protein as an antigen, another protein that is specifically bonded thereto, and a nucleic acid having a base sequence that hybridizes to the nucleic acid.

Specific examples of the biological substance recognition site include an anti-HER2 antibody specifically bonded to HER2 as a protein present on a cell surface, an anti-ER antibody specifically bonded to an estrogen receptor (ER) present in a cell nucleus, and an anti-actin antibody specifically bonded to actin forming a cell skeleton.

Among these antibodies, an antibody in which the anti-HER2 antibody and the anti-ER antibody are bonded to a fluorescent substance-containing nanoparticle (fluorescent staining reagent) is preferable because the fluorescent staining reagent can be used for selecting a drug for breast cancer.

A form of bonding between the biological substance recognition site and the fluorescent substance-containing nanoparticle is not particularly limited, and examples thereof include a covalent bond, an ionic bond, a hydrogen bond, a coordinate bond, physical adsorption, and a chemical adsorption. A bond with a strong bonding force such as a covalent bond is preferable due to stability of the bond.

There may be an organic molecule bonding the biological substance recognition site and the fluorescent substance-containing nanoparticle to each other therebetween. For example, a polyethylene glycol chain can be used in order to suppress nonspecific adsorption with a biological substance, and SM(PEG)12 manufactured by Thermo Scientific Co., Ltd. can be used.

In a case where the biological substance recognition site is bonded to a fluorescent substance-containing silica nanoparticle, similar procedures can be applied to a case where the fluorescent substance is a fluorescent organic dye and a case where the fluorescent substance is a quantum dot.

For example, a silane coupling agent which is a compound widely used for bonding an inorganic material to an organic material can be used. This silane coupling agent is a compound having an alkoxysilyl group that gives a silanol group by hydrolysis at one end of a molecule and a functional group such as a carboxyl group, an amino group, an epoxy group, or an aldehyde group at the other end, and is bonded to an inorganic substance via an oxygen atom of the silanol group.

Specific examples thereof include mercaptopropyltriethoxysilane, glycidoxypropyltriethoxysilane, aminopropyltriethoxysilane, and a silane coupling agent having a polyethylene glycol chain (for example, PEG-silane no. SIM 6492.7 manufactured by Gelest Inc.).

In a case where a silane coupling agent is used, two or more kinds thereof may be used in combination.

As reaction procedures between the fluorescent organic dye-containing silica nanoparticle and the silane coupling agent, a known method can be used.

For example, an obtained fluorescent organic dye-containing silica nanoparticle is dispersed in pure water, aminopropyltriethoxysilane is added thereto, and the resulting mixture is caused to react at room temperature for 12 hours. After completion of the reaction, a fluorescent organic dye-containing silica nanoparticle having a surface modified with an aminopropyl group can be obtained by centrifugation or filtration. Subsequently, by causing an amino group to react with a carboxyl group in an antibody, the antibody can be bonded to the fluorescent organic dye-containing silica nanoparticle via an amide bond. A condensing agent such as 1-ethyl-3-[3-dimethylaminopropyl] carbodiimide hydrochloride (EDC: manufactured by Pierce (registered trademark) Corporation) can also be used, if necessary.

A linker compound having a site that can be directly bonded to a fluorescent organic dye-containing silica nanoparticle modified with an organic molecule and a site that can be bonded to a molecular target substance can be used, if necessary. As a specific example, if sulfosuccinimidyl 4[N-maleimidomethyl]-cyclohexane-1-carboxylate (sulfo-SMCC: manufactured by Pierce Corporation) having both a site selectively reacting with an amino group and a site selectively reacting with a mercapto group is used, by bonding an amino group of a fluorescent organic dye-containing silica nanoparticle modified with aminopropyltriethoxysilane to a mercapto group in an antibody, an antibody-bonded fluorescent organic dye-containing silica nanoparticle can be obtained.

In a case where a biological substance recognition site is bonded to a fluorescent substance-containing polystyrene nanoparticle, similar procedures can be applied to a case where the fluorescent substance is a fluorescent organic dye and a case where the fluorescent substance is a quantum dot. That is, by impregnating a polystyrene nanoparticle having a functional group such as an amino group with a fluorescent organic dye or a quantum dot, it is possible to obtain a fluorescent substance-containing polystyrene nanoparticle having a functional group. Thereafter, by using EDC or sulfo-SMCC, an antibody-bonded fluorescent substance-including polystyrene nanoparticle can be obtained.

Examples of the biological substance recognition site include an antibody that recognizes a specific antigen such as M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular weight), pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, a factor VIII-related antigen, fascin, FSH, galectin-3, gastrin, GFAP, glucagon, glycophorin A, granzyme B, hCG, hGH, *Helicobacter pylori*, an HBc antigen, an HBs antigen, a hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, P63, PAX 5, PLAP, *Pneumocystis carinii*, podoplanin (D2-40), PGR, prolactin, PSA, prostatic acid phosphatase, Renal Cell Carcinoma, S100, somatostatin, spectrin, synaptophysin, TAG-72, TdT, thyroglobulin, TSH, TTF-1, TRAcP, tryptase, villin, vimentin, WT1, or Zap-70.

Incidentally, as described above, the fluorescent substance or the fluorescent substance-containing nanoparticle is used by being directly bonded to the biological substance recognition site in advance. In addition, the fluorescent substance or the fluorescent substance-containing nanoparticle may be indirectly bonded to the biological substance recognition site in a staining step as in a known indirect method in immunostaining. Specifically, for example, staining may be performed by utilizing the following fact. That is, a tissue sample is caused to react with a biotinylated primary antibody having a specific biological substance as an antigen, then the tissue sample is caused to further react with a staining reagent bonded to a fluorescent substance or a fluorescent substance-containing nanoparticle modified with streptavidin, and streptavidin and biotin are specifically bonded to each other to form a complex. In addition, for example, staining may be performed by causing a tissue sample to react with a primary antibody having a specific protein as an antigen, causing the tissue sample to further react with a biotinylated secondary antibody having the primary antibody as an antigen, and then causing the tissue sample to react with a fluorescent substance or a fluorescent substance-containing nanoparticle modified with streptavidin.

(4) Staining Method

A method for manufacturing a tissue section is not particularly limited, and a tissue section manufactured by a known method can be used. The following staining method is not limited to a pathological tissue section but can also be applied to a cultured cell.

(4.1) Deparaffinization Step

A tissue section is immersed in a container containing xylene to remove paraffin. Temperature is not particularly limited but can be room temperature. Immersion time is preferably 3 minutes or more and 30 minutes or less. Xylene may be exchanged during immersion, if necessary.

Subsequently, the tissue section is immersed in a container containing ethanol to remove xylene. Temperature is not particularly limited but can be room temperature. Immersion time is preferably 3 minutes or more and 30 minutes or less. Ethanol may be exchanged during immersion, if necessary.

Subsequently, the tissue section is immersed in a container containing water to remove ethanol. Temperature is not particularly limited but can be room temperature. Immersion time is preferably 3 minutes or more and 30 minutes or less. Water may be exchanged during immersion, if necessary.

(4.2) Activation Treatment

An activation treatment of a biological substance of a tissue section is performed according to a known method.

Activation conditions are not particularly defined. However, as an activating solution, a 0.01M citric acid buffer solution (pH 6.0), a 1 mM EDTA solution (pH 8.0), 5% urea, a 0.1M tris-hydrochloric acid buffer solution, and the lie can be used. An autoclave, a microwave, a pressure cooker, a water bath, or the like can be used as a heating device. Temperature is not particularly limited but can be room temperature. Temperature can be 50 to 130 degrees, and time can be 5 to 30 minutes.

Subsequently, a tissue section after the activation treatment is immersed in a container containing phosphate buffered saline (PBS) and washed. Temperature is not particularly limited but can be room temperature. Immersion time is preferably 3 minutes or more and 30 minutes or less. PBS may be exchanged during immersion, if necessary.

(4.3) Staining with Fluorescent Staining Reagent

A PBS dispersion of a fluorescent staining reagent is placed on a tissue section and reacted with a biological substance of the tissue section.

By changing a biological substance recognition site of the fluorescent staining reagent, staining corresponding to various biological substances is possible. In a case where a fluorescent substance-containing nanoparticle bonded to several kinds of biological substance recognition sites is used as a fluorescent staining reagent, fluorescent substance-containing nanoparticle PBS dispersions may be mixed in advance, or each of the dispersions may be sequentially placed on a tissue section. Temperature is not particularly limited but can be room temperature. Reaction time is preferably 30 minutes or more and 24 hours or less.

Before dyeing with a fluorescent staining reagent is performed, it is preferable to drop a known blocking agent such as BSA-containing PBS.

Subsequently, the stained tissue section is immersed in a container containing PBS to remove an unreacted fluorescent substance-containing nanoparticle. Temperature is not particularly limited but can be room temperature. Immersion time is preferably 3 minutes or more and 30 minutes or less. PBS may be exchanged during immersion, if necessary. A cover glass is placed on a tissue section for encapsulation. A commercially available encapsulating agent may be used, if necessary.

Incidentally, in a case where HE staining using an HE staining reagent or the like is performed in order to obtain a form image, staining is performed before encapsulation with a cover glass.

(5) Acquisition of Fluorescent Image

A microscopic image (fluorescent image) of the stained tissue section is acquired using the microscopic image acquisition device 1A. In the microscopic image acquisition device 1A, an excitation light source and an optical filter for fluorescence detection corresponding to an absorption maximum wavelength and a fluorescence wavelength of a fluorescent substance used for a fluorescent staining reagent are selected.

<Operation of Diagnosis Support Information Generation System 100 (Including Image Processing Method)>

Hereinafter, an operation of acquiring a form image representing a form of a cell and an image representing expression of a specific biological substance in a cell and performing analysis in a diagnosis support information generation system 100 will be described with reference to specific embodiments. However, the present invention is not limited to the following embodiments.

The image analysis processing of the present invention is executed by cooperation between the control unit 21 and an image processing program stored in the storage unit 25. The control unit 21 executes processing described in the following embodiments according to the image processing program.

First Embodiment

In the first embodiment, using a section of a breast cancer tissue which has been subjected to HE staining and staining with a Ki67 protein using a fluorescent substance-containing nanoparticle as a tissue sample, a region stained in blue-violet by HE staining is extracted as a candidate region, and a region of a cell nucleus of a cancer cell in the breast cancer tissue is extracted as a diagnosis target region from the candidate region.

It is known that the Ki67 protein (hereinafter, referred to as "specific protein") is expressed at a high concentration in a cell nucleus of a cancer cell, for example.

As a form image representing a form of a predetermined structure of a cell, a bright field image is acquired. As an image representing expression of a specific biological substance (in this case, a specific protein) in a cell, a fluorescent image is acquired.

First, an operator stains a tissue section using an HE staining reagent and a fluorescent staining reagent (fluorescent substance-containing nanoparticle bonded to an anti-Ki67 antibody).

Thereafter, using the microscopic image acquisition device 1A, a bright field image and a fluorescent image are acquired according to procedures of (a1) to (a5).

(a1) An operator places a tissue section stained with an HE staining reagent and a fluorescent staining reagent on a slide and places the slide on a slide fixing stage of the microscopic image acquisition device 1A.

(a2) A unit is set to a bright field unit, photographing magnification and focus are adjusted, and the region of an observation target on the tissue section is put in a field of view.

(a3) Photographing is performed by imaging means to generate image data of the bright field image, and the image data is transmitted to the image processing device 2A.

(a4) The unit is changed to a fluorescent unit.

(a5) Photographing is performed by the imaging means without changing the field of view and the photographing magnification to generate image data of a fluorescent image, and the image data is transmitted to the image processing device 2A.

According to the above image acquisition method, a fluorescent image and a form image obtained by photographing almost the same range of a tissue section are obtained. However, the fluorescent image and the form image are not limited to images obtained by photographing the same range but are only required to be overlapped with each other at least in a part of the photographed region. Specifically, for example, a fluorescent image obtained by photographing a narrow region in a tissue section and a form image obtained by photographing a wide range including the region in which the fluorescent image has been photographed are acquired, the form image and the fluorescent image are aligned with each other by a known method, and then image analysis processing described below may be performed.

Thereafter, using the image processing device 2A, image analysis processing is executed based on the bright field image and the fluorescent image.

FIG. 3 illustrates a flowchart of image analysis processing in the image processing device 2A of the first embodiment.

First, if a bright field image (form image) from the microscopic image acquisition device 1A is input by the communication I/F 24 (step S11), a region of a cell nucleus stained in blue-violet is extracted from the bright field image (step S12: first extraction step).

In step S12, as illustrated in FIG. 4, for example, the bright field image is converted into a monochrome image (step S121), the monochrome image is subjected to threshold processing with a predetermined threshold to binarize a value of each pixel (step S122), and the binary image is subjected to noise processing (step S123).

Specifically, the noise processing can be performed by subjecting the binary image to closing processing. The closing processing performs contraction processing by the same number of times after expansion processing is performed. The expansion processing replaces a pixel of interest with white in a case where at least one white pixel is included in pixels within a range of n×n pixels (n is an integer of 2 or more) from the pixel of interest. The contraction processing replaces a pixel of interest with black in a case where at least one black pixel is included in pixels within a range of n×n pixels from the pixel of interest. The closing processing can remove a small region such as noise.

In steps S121 to S123, an image (candidate region image) in which a candidate region (region of a cell nucleus in the present embodiment) has been extracted from a bright field image is generated.

Subsequently, characteristic information indicating characteristics of the extracted candidate region is extracted (step S124).

The characteristic information is arbitrary as long as being information on a candidate region, but includes, for example, any one of the size (area, peripheral length, length of short diameter, length of long diameter, or the like) of the candidate region, the shape (circularity, ratio between short diameter and long diameter, or the like) thereof, the position thereof, and the distribution thereof.

The definition of the circularity is arbitrary. However, for example, in a case where the area of a cell nucleus is represented by S and the circumferential length thereof is represented by L, as a value calculated by formula $4\pi S/L^2$ is closer to 1, the shape is closer to a circle and can be defined as higher circularity. In addition, if a convex hull area ratio which is a ratio between the area of a candidate region and the area of a convex hull region of the candidate region is calculated and is close to 1, the shape may be defined as high circularity.

The position can be defined as, for example, the coordinates of the center of gravity of a candidate region.

The distribution can be defined as, for example, a distance from an adjacent candidate region or the density of a candidate region in a bright field image.

Meanwhile, if a fluorescent image from the microscopic image acquisition device 1A is input by the communication I/F 24 (step S13), a fluorescent bright spot is extracted from the fluorescent image, and biological substance information on a specific protein is acquired (step S14: acquisition step).

In step S14, as illustrated in FIG. 5, a color component corresponding to the wavelength of a fluorescent bright spot is extracted from a fluorescent image (step S141), and the fluorescent image after the color component extraction is subjected to threshold processing to generate a binary image (fluorescent bright spot image) from which the fluorescent bright spot has been extracted (step S142).

In step S141, only a fluorescent bright spot in which the brightness of an emission wavelength component of fluorescent particles used for staining is equal to or larger than a predetermined threshold is extracted. Before the threshold processing in step S142, processing for removing noise such as cell autofluorescence or another unnecessary signal component may be performed.

In steps S141 and S142, an image (fluorescent bright spot image) from which a fluorescent bright spot has been extracted is generated.

Subsequently, in step S143, biological substance information based on a fluorescent bright spot is acquired. The biological substance information is, for example, information on the position (coordinates) of a fluorescent bright spot in an image.

After step S14, a candidate region image is added to a fluorescent bright spot image, and a candidate region and a fluorescent bright spot are superimposed on each other (step S15).

Subsequently, a diagnosis target region is extracted from the candidate region based on characteristic information of the candidate region (step S16: second extraction step).

Specifically, in step S16, the control unit 21 reads data of characteristics such as the area and the shape of a diagnostic target cell stored in the storage unit 25 in advance, compares the data with the characteristic information of the candidate region, and determines whether the candidate region is a diagnosis target region.

Figure 6:
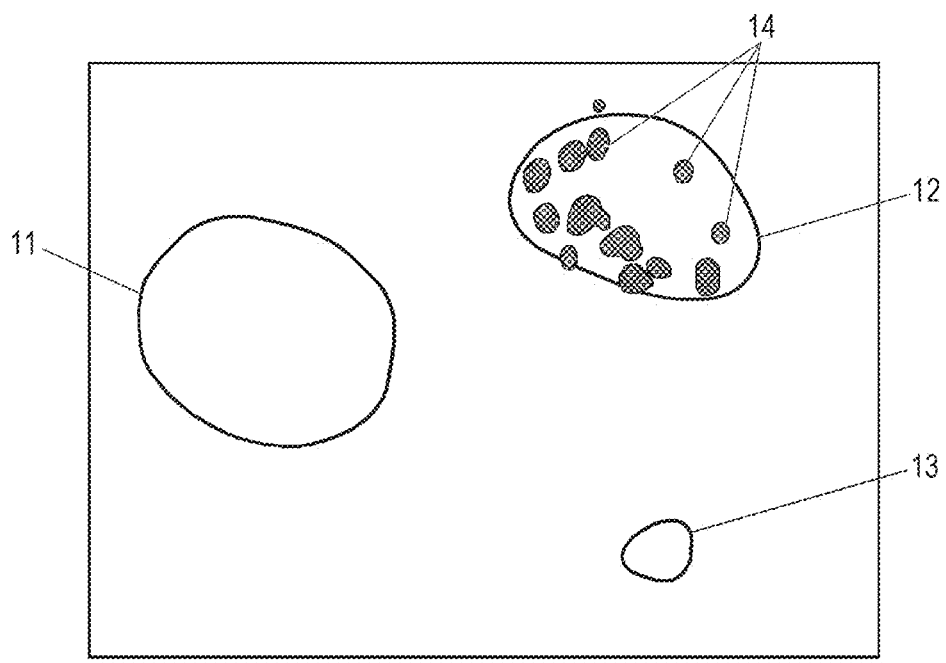
FIG. 6 is a schematic diagram of an image obtained by superimposition in step S15 of the first embodiment.

FIG. 6 is an example of a schematic diagram of an image obtained by superimposition in step S15 and illustrates candidate regions 11 to 13 extracted in step S12 and a fluorescent bright spot 14 extracted in step S14

In step S16, the candidate regions 11 and 12 are determined to be cancer cells as a diagnosis target based on the area, the shape, and the like of the candidate region, and are extracted as diagnosis target regions. Meanwhile, in step S16, the candidate region 13 having a small area is considered not to be a cancer cell but to be, for example, a fibroblast which is an interstitial tissue, and therefore is not extracted as a diagnosis target region.

In step S17 (creation step), diagnosis support information such as the number of a specific protein per cell, the density thereof, or the distribution thereof is created based on the biological substance information in the diagnosis target region extracted in step S16.

Second Embodiment

Hereinafter, an operation of a diagnosis support information generation system 100 of a second embodiment will be described. A tissue sample similar to that in the first embodiment is used.

Figure 7:
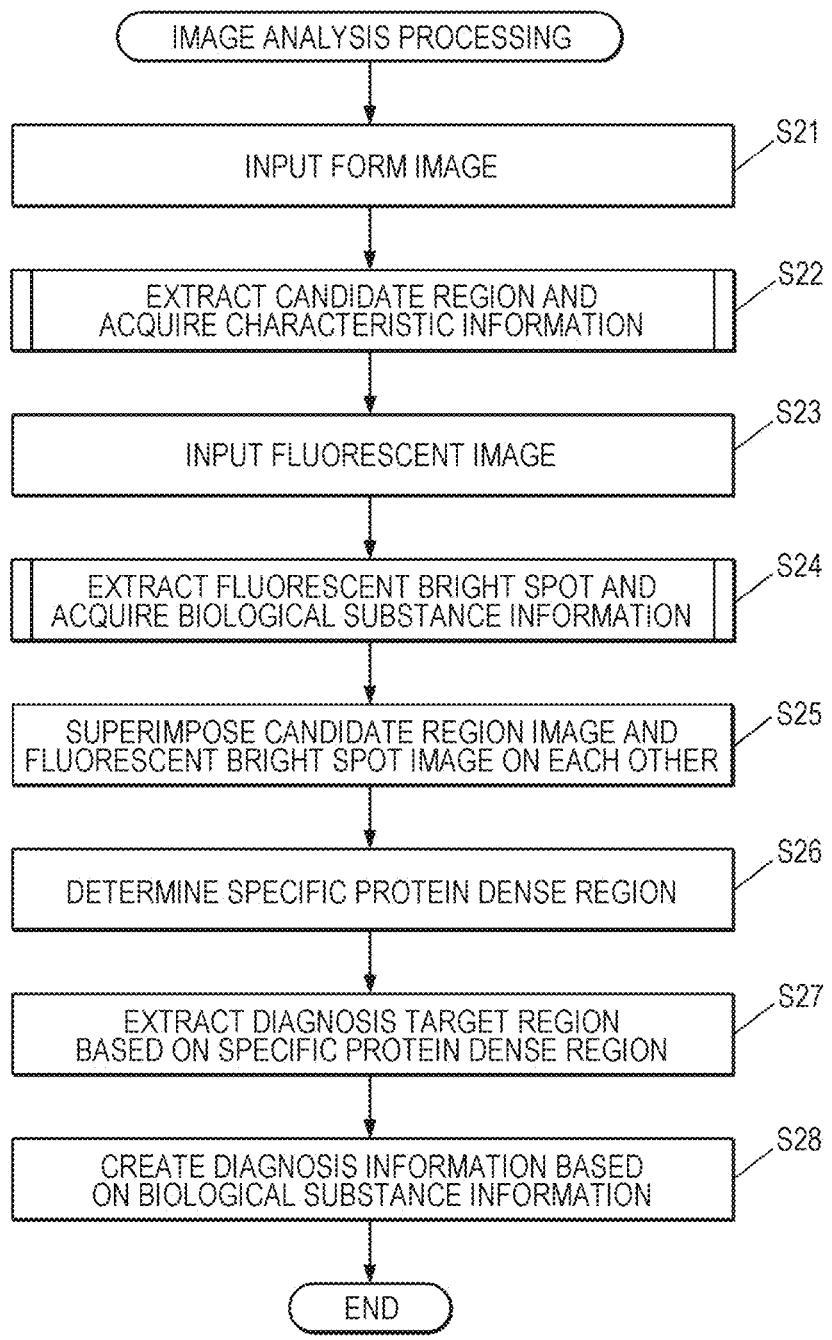
FIG. 7 is a flowchart illustrating image analysis processing in a second embodiment.

FIG. 7 illustrates a flowchart of image analysis processing in the second embodiment. Steps S21 to S25 are performed in a similar manner to steps S11 to S15 of the first embodiment.

In steps S26 and S27 (second extraction step) of the second embodiment, a diagnosis target region is extracted from a candidate region based on biological substance information acquired in step S24 (acquisition step).

Examples of the biological substance information used in the second extraction step of the second embodiment include the position of a fluorescent bright spot in an image, the number of fluorescent bright spots per candidate region, and the density thereof.

Figure 8:
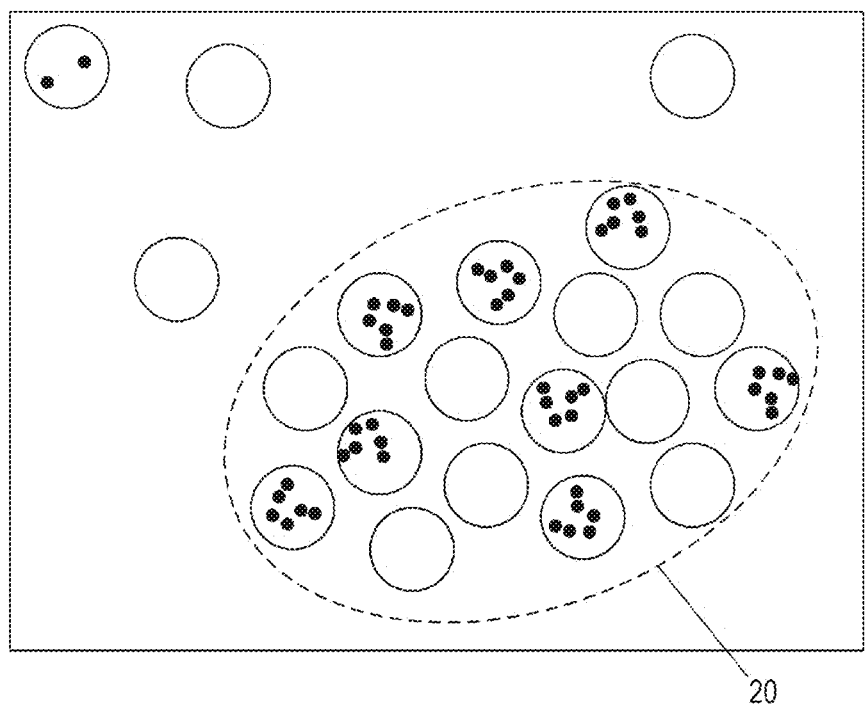
FIG. 8 is a schematic diagram of an image obtained by superimposition in step S25 of the second embodiment.

FIG. 8 illustrates an example of a schematic diagram of an image obtained in step S25. In FIG. 8, a white circle indicates a candidate region, and a black circle indicates a fluorescent bright spot. In step S26 of the second embodiment, a specific protein dense region 20 (the region surrounded by the dotted line in FIG. 8) in which fluorescent bright spots are relatively densely present is determined. A method for determining the degree of denseness of the fluorescent bright spots is arbitrary. For example, in a case where candidate regions each including a predetermined number or more of fluorescent bright spots are concentrated close to each other, a region including these close candidate regions is determined to be the specific protein dense region 20.

Subsequently, in step S27, a candidate region in the specific protein dense region 20 is determined to be a diagnosis target and is extracted as a diagnosis target region. Even if a candidate region apart from the specific protein dense region 20 by a predetermined distance or more includes a fluorescent bright spot, the candidate region is determined not to be a diagnosis target and is not extracted as a diagnosis target region.

In step S28 (creation step), diagnosis support information such as the number of specific proteins per cell, the density thereof, or the distribution thereof is created based on the biological substance information in the diagnosis target region extracted in step S27.

In order to extract a diagnosis target region in the second embodiment, it is necessary to observe, in an image, a fluorescent bright spot representing expression of a specific protein in a certain amount. However, in the following cases, for example, the method for extracting a diagnosis target region in the second embodiment is particularly suitable.

In diagnosis of colorectal cancer or stomach cancer, the depth of cancer cells infiltrated from a surface of a specimen is important when the specimen is collected, and generally, a cell apart from a region where the cancer cells are concentrated is not used as a diagnosis target. Therefore, in such a case, preferably, a cell in the specific protein dense region is used as a diagnosis target, and a cell apart from the specific protein dense region is not used as a diagnosis target.

Third Embodiment

In the following third embodiment, using a section of a breast cancer tissue which has been subjected to HE staining and staining with a first biological substance and a second biological substance (specific protein) using a fluorescent substance-containing nanoparticle as a tissue sample, a region stained in blue-violet by HE staining is extracted as a candidate region, and a region of a cell nucleus of a cancer cell is extracted as a diagnosis target region from the candidate region.

In the third embodiment, for example, the first biological substance is a 112 kDa protein known to be expressed in a fibroblast which is an interstitial tissue, and the second biological substance (specific protein) is a Ki67 protein expressed in a cell nucleus.

The fluorescent substance-containing nanoparticle used for staining the first biological substance and the second biological substance is selected such that fluorescence emitted by one is not excitation light of the other.

As a form image representing a form of a predetermined structure of a cell, a bright field image is acquired. As an image representing expression of a specific biological substance (in this case, the first biological substance and the second biological substance) in a cell, a fluorescent image is acquired.

First, an operator stains a tissue section using an HE staining reagent and a fluorescent staining reagent (fluorescent substance-containing nanoparticle bonded to antibodies of the first biological substance and the second biological substance).

Thereafter, using the microscopic image acquisition device 1A, a bright field image and a fluorescent image are acquired according to procedures of (a1) to (a6).

(a1) An operator places a tissue section stained with an HE staining reagent and a fluorescent staining reagent on a slide and places the slide on a slide fixing stage of the microscopic image acquisition device 1A.

(a2) A unit is set to a bright field unit, photographing magnification and focus are adjusted, and the region of an observation target on the tissue section is put in a field of view.

(a3) Photographing is performed by imaging means to generate image data of the bright field image, and the image data is transmitted to the image processing device 2A.

(a4) The unit is changed to a fluorescent unit.

(a5) Photographing is performed by the imaging means without changing the field of view and the photographing magnification to generate image data of a first fluorescent image representing expression of the first biological substance, and the image data is transmitted to the image processing device 2A.

(a6) Photographing is performed by the imaging means without changing the field of view and the photographing magnification while excitation light and a filter are changed to generate image data of a second fluorescent image representing expression of the second biological substance, and the image data is transmitted to the image processing device 2A.

Thereafter, in the image processing device 2A, image analysis processing is executed based on the bright field image, the first fluorescent image, and the second fluorescent image.

Figure 9:
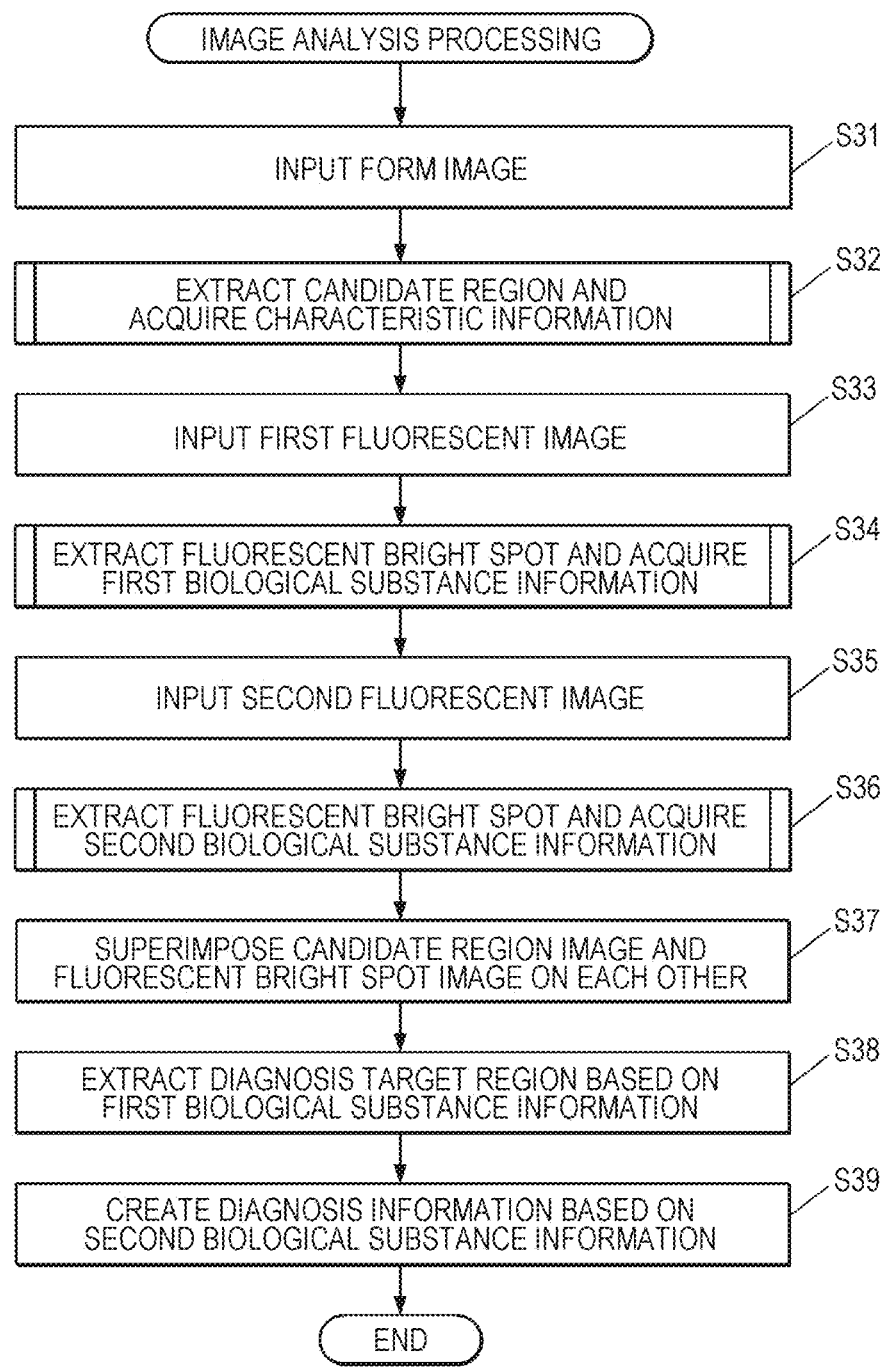
FIG. 9 is a flowchart illustrating image analysis processing in a third embodiment.

FIG. 9 illustrates a flowchart of image analysis processing in the third embodiment.

Steps S31 and S32 (first extraction step) are performed in a similar manner to steps S11 and S12 of the first embodiment.

Steps S33 and S34 (acquisition steps) and steps S35 and S36 (acquisition steps) are performed on the first fluorescent image acquired in (a5) and the second fluorescent image acquired in (a6), input from the microscopic image acquisition device 1A by the communication I/F 24, respectively, in a similar manner to steps S13 and S14 in the first embodiment.

After step S36, a candidate region (cell nucleus) image is added to a fluorescent bright spot image representing expression of each of the first biological substance and the second biological substance, and the candidate region and the fluorescent bright spot are superimposed on each other (step S37).

Subsequently, a diagnosis target region is extracted from the candidate region based on the biological substance information on the first biological substance acquired in step S34 (step S38: second extraction step).

Specifically, in step S38, it is determined whether the candidate region is a diagnosis target region based on whether the first biological substance is included in each candidate region.

Figure 10:
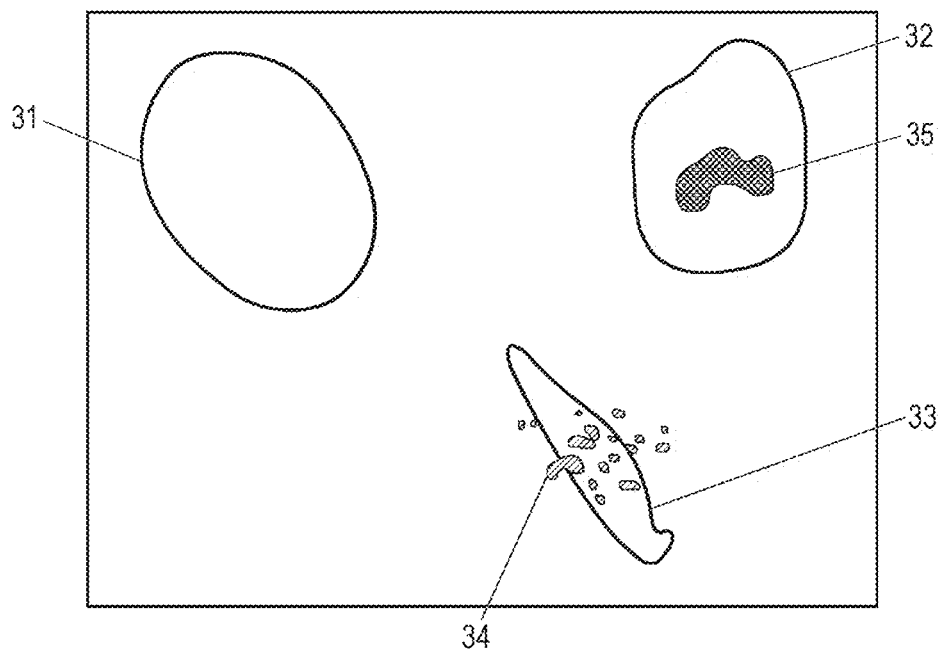
FIG. 10 is a schematic diagram of an image obtained by superimposition in step S37 of the third embodiment.

FIG. 10 is an example of a schematic diagram of the image obtained by superimposition in step S37, in which candidate regions 31 to 33 extracted in step S32, a fluorescent bright spot 34 representing expression of the first biological substance extracted in step S34, and a fluorescence bright spot 35 representing expression of the second biological substance extracted in step S36 are observed.

In step S38, expression of a 112 kDa protein expressed in a fibroblast is not observed in the candidate regions 31 and 32, and therefore the candidate regions 31 and 32 are determined to be cancer cells as a diagnosis target and are extracted as diagnosis target regions. Meanwhile, in step S38, the candidate region 33 in which the fluorescent bright spot 34 representing expression of a 112 kDa protein expressed in a fibroblast is observed is determined not to be a cancer cell but to be a fibroblast, and therefore the candidate region 33 is not extracted as a diagnosis target region.

In step S39 (creation step), diagnosis support information such as the number of the second biological substance per cell, the density thereof, or the distribution thereof is created based on the biological substance information on the second biological substance in the diagnosis target region extracted in step S38.

Modification of Third Embodiment

Image analysis processing in a modification of the third embodiment is performed in a similar manner to the image analysis processing (refer to the flowchart of FIG. 9) in the third embodiment. The modification of the third embodiment will be described by taking a case where CEA is used as the first biological substance of the third embodiment as an example. CEA is known as a marker of an epithelial cancer cell.

Details of steps S31 to S37 in the modification of the third embodiment are similar to steps S31 to S37 of the third embodiment except that CEA is used as the first biological substance.

In step S38 (second extraction step) of the modification of the third embodiment, a diagnosis target region is extracted from the candidate region based on the biological substance information on the first biological substance (CEA) acquired in step S34.

Specifically, in step S38 in the modification of the third embodiment, it is determined whether the candidate region is a diagnosis target region based on whether CEA is included in each candidate region.

Figure 11:
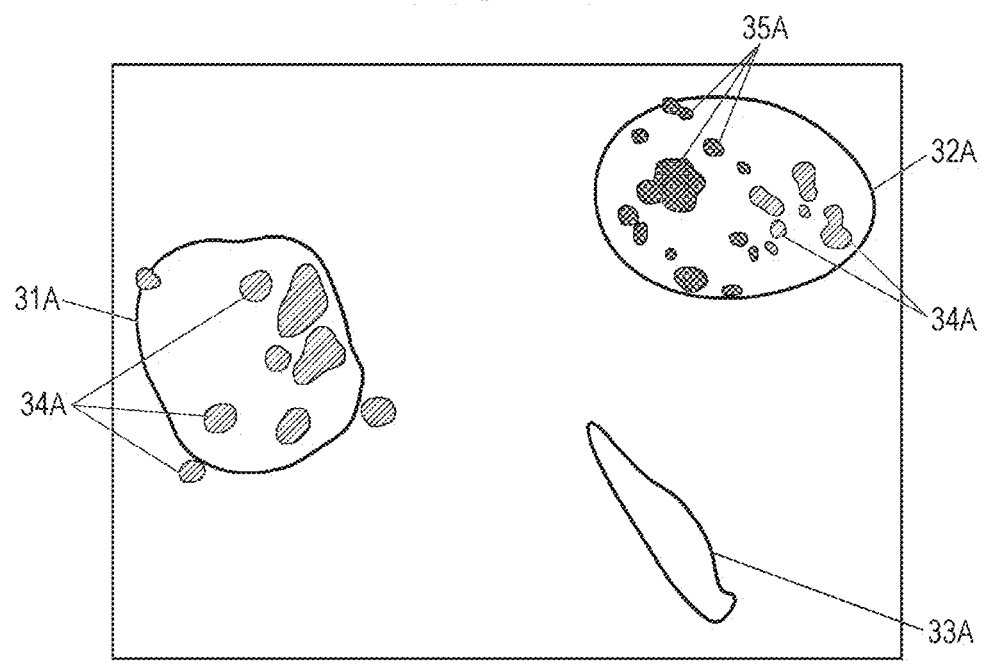
FIG. 11 is a schematic diagram of an image obtained by superimposition in step S37 of a modification of the third embodiment.

FIG. 11 is an example of a schematic diagram of the image obtained by superimposition in step S37, in which candidate regions 31A to 33A extracted in step S32 (first extraction step), a fluorescent bright spot 34A representing expression of CEA extracted in step S34 (acquisition step), and a fluorescence bright spot 35A representing expression of the second biological substance extracted in step S36 (acquisition step) are observed.

Expression of CEA (fluorescent bright spot 34A) is observed in the candidate regions 31A and 32A. Therefore, in step S38, the candidate regions 31A and 32A are determined to be cancer cells as a diagnosis target and are extracted as diagnosis target regions. Meanwhile, in step S38, the candidate region 33A in which expression of CEA is not observed is determined not to be a cancer cell but to be a fibroblast, and therefore is not extracted as a diagnosis target region.

Step S39 (creation step) of the modification of the third embodiment is performed in a similar manner to step S39 of the third embodiment.

Fourth Embodiment

Hereinafter, an operation of a diagnosis support information generation system 100 of a fourth embodiment will be described. Description will be made on the assumption that a tissue sample similar to that in the third embodiment is used.

Figure 12:
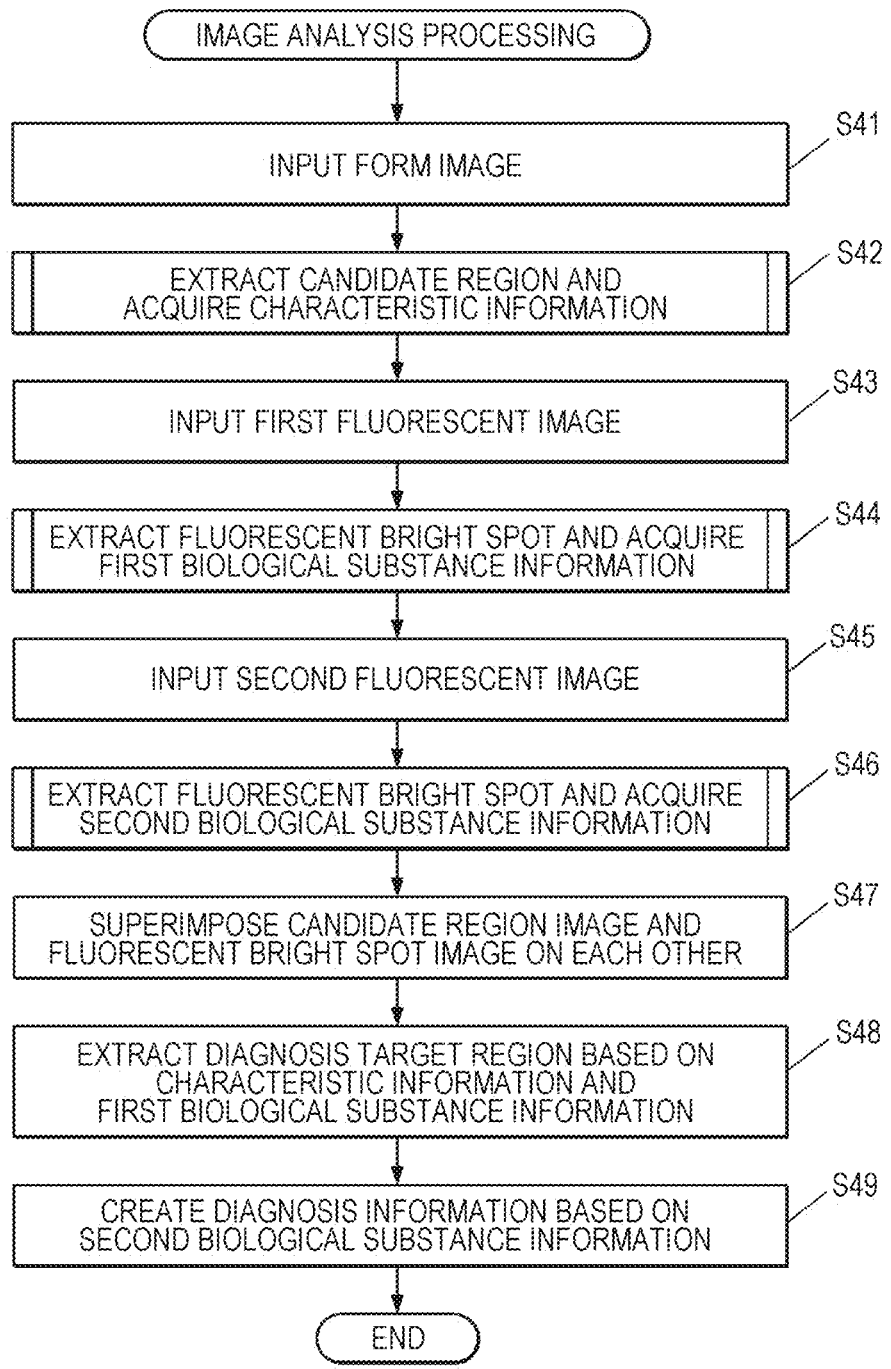
FIG. 12 is a flowchart illustrating image analysis processing in a fourth embodiment.

FIG. 12 illustrates a flowchart of image analysis processing in the fourth embodiment.

Steps S41 to S47 are performed in a similar manner to steps S31 to S37 of the third embodiment.

In step S48 (second extraction step) of the fourth embodiment, a diagnosis target region is extracted from the candidate region based on the characteristic information of the candidate region acquired in step S42 (first extraction step) and the biological substance information on the first biological substance acquired in step S44 (acquisition step).

Specifically, for example, in step S48, first, a candidate region determined to be a diagnosis target region based on the characteristic information of the candidate region is extracted in a similar manner to step S16 of the first embodiment. Subsequently, it is further determined whether the candidate region is a diagnosis target region based on whether the first biological substance is included in the extracted candidate region in a similar manner to step S38 of the third embodiment.

Figure 13:
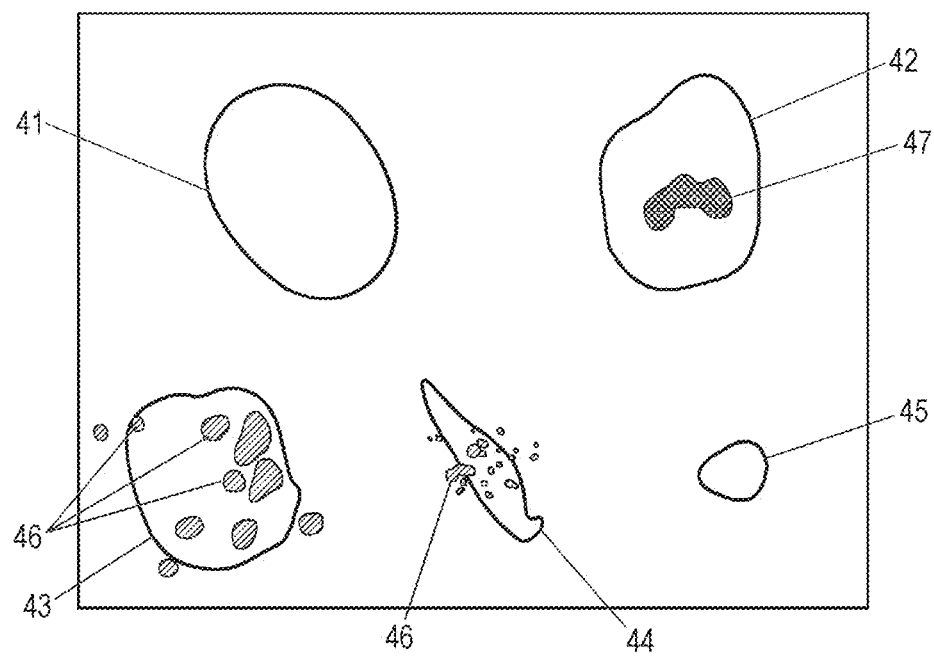
FIG. 13 is a schematic diagram of an image obtained by superimposition in step S47 of the fourth embodiment.

FIG. 13 is an example of a schematic diagram of the image obtained by superimposition in step S47, in which candidate regions 41 to 45 extracted in step S42, a fluorescent bright spot 46 representing expression of the first biological substance extracted in step S44, and a fluorescence bright spot 47 representing expression of the second biological substance extracted in step S46 (acquisition step) are observed.

In step S48, first, the candidate regions 41 and 43 are determined to be cancer cells as a diagnosis target based on the area and the shape of the candidate region and are extracted. Meanwhile, the candidate region 44 having a low circularity and the candidate region 45 having a small area are determined not to be cancer cells, and therefore are not extracted.

Subsequently, among the extracted candidate regions 41 to 43, in the candidate regions 41 and 42, a fluorescent bright spot 46 representing expression of a 112 kDa protein expressed in a fibroblast is not observed. Therefore, the candidate regions 41 and 42 are determined to be cancer cells as a diagnosis target and extracted as diagnosis target regions. Meanwhile, in step S48, the candidate region 43 in which a fluorescent bright spot representing expression of a 112 kDa protein expressed in a fibroblast is observed is determined not to be a cancer cell but to be a fibroblast, and therefore the candidate region 43 is not extracted as a diagnosis target region.

In step S49 (creation step), diagnosis support information such as the number of the second biological substance per cell, the density thereof, or the distribution thereof is created based on the biological substance information on the second biological substance in the diagnosis target region extracted in step S48.

According to the first to fourth embodiments described above, a diagnosis target region excluding a cell that is not a diagnosis target is extracted from a candidate region based on characteristic information and/or biological substance information on cells.

This makes it possible to create diagnosis support information based on expression of a biological substance in a diagnosis target region. Therefore, expression of a specific protein in a cell as an observation target can be accurately quantified, and accuracy of diagnosis is improved.

Note that the description contents in the above embodiments are preferable examples of the present invention, and the present invention is not limited thereto.

In the above embodiments, the diagnosis support information is created based on only one kind of specific protein, but two or more kinds of fluorescent particles having different emission wavelengths for a plurality of specific proteins may be used.

In the above embodiments, the Ki67 protein in breast cancer is described as an example of the specific protein, but the present invention is not limited thereto. If a biological substance recognition site at the time of acquiring a fluorescent image is changed according to the kind of a lesion (cancer) as a diagnosis target, a characteristic quantity quantitatively indicating an expression quantity of a specific protein according to the kind of a lesion can be provided to a doctor.

The above description discloses an example in which an HDD, a semiconductor nonvolatile memory, or the like is used as a computer readable medium of the program according to the present invention, but the present invention is not limited to this example. As another computer readable medium, a portable recording medium such as a CD-ROM can be applied. As a medium for providing data of the program according to the present invention via a communication line, a carrier wave is also applied.

Besides, the detailed configuration and the detailed operation of each device constituting the diagnosis support information generation system 100 can be appropriately changed without departing from the gist of the invention.

INDUSTRIAL APPLICABILITY

The present invention is characterized by being capable of accurately extracting a cell region as a diagnosis target and can be particularly preferably used for generation of highly accurate pathological diagnosis information.

REFERENCE SIGNS LIST

1A Microscopic image acquisition device
2A Image processing device
21 Control unit
22 Operation unit
23 Display unit
24 Communication I/F
25 Storage unit
26 Bus
3A Cable
11 to 13 Candidate region
14 Fluorescent bright spot
20 Specific protein dense region
31 to 33 Candidate region
34, 35 Fluorescent bright spot
31A to 33A Candidate region
34A, 35A Fluorescent bright spot
41 to 45 Candidate region
46, 47 Fluorescent bright spot
100 Diagnosis support information generation system

The invention claimed is:

1. An image processing device comprising:
   first extraction means for extracting a candidate region from a form image representing a form of a cell in a tissue sample;
   acquisition means for acquiring biological substance information on at least one kind of the biological substance from an image representing expression of one or more kinds of biological substances in the tissue sample; and
   second extraction means for extracting a diagnosis target region from the candidate region based on characteristic information indicating characteristics of the candidate region and/or the biological substance information;
   wherein
      the second extraction means extracts the diagnosis target region based on at least the biological substance information, and
      the biological substance information includes at least one of a position, the number, and density of the biological substance.

2. The image processing device according to claim 1, wherein
   the second extraction means extracts the diagnosis target region based on at least the characteristic information, and
   the characteristic information includes at least one of a shape, an area, and a position of the candidate region.

3. The image processing device according to claim 1, wherein
   the acquisition means acquires biological substance information on the plurality of kinds of biological substances from the images representing expression of the plurality of kinds of biological substances in the tissue sample, and
   the second extraction means extracts the diagnosis target region based on at least the biological substance information on a first biological substance.

4. The image processing device according to claim 1, further comprising creation means for creating diagnosis support information in the diagnosis target region extracted by the second extraction means based on the biological substance information.

5. The image processing device according to claim 3, further comprising creation means for creating diagnosis support information in the diagnosis target region extracted by the second extraction means based on the biological substance information on a second biological substance.

6. A non-transitory recording medium storing a computer readable program for causing a computer to function as:
   a first extractor that extracts a candidate region from a form image representing a form of a cell in a tissue sample;
   an acquisitor that acquires biological substance information on at least one kind of the biological substance from an image representing expression of one or more kinds of biological substances in the tissue sample; and
   a second extractor that extracts a diagnosis target region from the candidate region based on characteristic information indicating characteristics of the candidate region and/or the biological substance information;
   wherein
      the second extractor extracts the diagnosis target region based on at least the biological substance information, and
      the biological substance information includes at least one of a position, the number, and density of the biological substance.

7. The image processing device according to claim 2, wherein
   the acquisitor acquires biological substance information on the plurality of kinds of biological substances from the images representing expression of the plurality of kinds of biological substances in the tissue sample, and
   the second extractor extracts the diagnosis target region based on at least the biological substance information on a first biological substance.

8. The image processing device according to claim 2, further comprising a creator that creates diagnosis support information in the diagnosis target region extracted by the second extractor based on the biological substance information.

9. The image processing device according to claim 1, wherein
   the acquisitor acquires biological substance information on the plurality of kinds of biological substances from the images representing expression of the plurality of kinds of biological substances in the tissue sample, and
   the second extractor extracts the diagnosis target region based on at least the biological substance information on a first biological substance.

10. The image processing device according to claim 1, further comprising a creator that creates diagnosis support information in the diagnosis target region extracted by the second extractor based on the biological substance information.

* * * * *